United States Patent [19]

Mitchinson et al.

[11] Patent Number: 5,652,127
[45] Date of Patent: Jul. 29, 1997

[54] METHOD FOR LIQUEFYING STARCH

[75] Inventors: Colin Mitchinson, Half Moon Bay, Calif.; Leif P. Solheim, Clinton, Iowa

[73] Assignee: Genencor International, Inc., Rochester, N.Y.

[21] Appl. No.: 459,984

[22] Filed: Jun. 2, 1995

[51] Int. Cl.⁶ .............................. C12P 19/14; C12M 9/24; C12M 9/26
[52] U.S. Cl. .............................. 435/99; 435/72; 435/201; 435/202; 435/203; 435/204; 435/205; 435/275
[58] Field of Search ....................... 435/99, 201, 72, 435/202, 203, 204, 275

[56] References Cited

U.S. PATENT DOCUMENTS

| | | | |
|---|---|---|---|
| 4,052,226 | 10/1977 | Verbanac | 435/99 |
| 4,511,654 | 4/1985 | Rohrbach et al. | 435/95 |
| 4,717,662 | 1/1988 | Montgomery et al. | 435/99 |
| 5,322,778 | 6/1994 | Antrim et al. | 435/99 |

OTHER PUBLICATIONS

D. Galabova and P. Velcheva (1985) *Acta Microbiologica Bulgarica* 16:67–71.

Primary Examiner—Michael G. Wityshyn
Assistant Examiner—L. Blaine Lankford
Attorney, Agent, or Firm—Kirsten A. Anderson

[57] ABSTRACT

According to the invention a method is provided for liquefying starch comprising the steps of adding a sodium composition to the starch prior to or simultaneously with liquefying the starch; adding α-amylase to the treated starch; and reacting the treated starch for a time and at a temperature effective to liquefy the treated starch. Preferred sodium compositions comprise sodium chloride, sodium bicarbonate, sodium benzoate, sodium sulfate, sodium bisulfite, sodium ascorbate, sodium acetate, sodium nitrate, sodium tartrate, sodium tetraborate, sodium propionate, sodium citrate, sodium succinate, monosodium glutamate, trisodium citrate, sodium phosphate or a mixture thereof.

10 Claims, No Drawings

METHOD FOR LIQUEFYING STARCH

BACKGROUND OF THE INVENTION

The present invention relates to modifying the use of α-amylase in conversion of grain starch to downstream products, such as dextrose, fructose and alcohol. In particular, the present invention relates to the addition of sodium ion to a starch mixture prior to or during liquefaction to increase the efficiency of liquefaction at low pH, i.e., at or below about pH5.9.

Grains such as corn have long been used as a source of starch. One of the well known methods of separating and purifying starch for use in industrial processes is the wet-milling process. This method has developed into a highly specific and integrated system designed to separate the major components of a grain kernel as completely as possible (see Stanley A. Watson, *Starch: Chemistry & Technology*, Vol. II, *Industrial Aspects*, Academic Press, New York, 1967, pp. 30–51).

In a common wet-milling process, dry grains used for the production of starch products are first subjected to a soaking process called steeping. During steeping, the grains are subjected to a counterflow water current which separates many solubles, including phytate and phytic acid, sugars, salts and proteins, from the grain granules. The steeped grains are separated from the soaking water (steepwater) and subjected to mechanical cracking and grinding procedures. Flotation and centrifugation techniques are then used to separate germ from the starch, fiber and protein. The resulting slurry of endosperm (starch), fiber and protein is then further ground and screened to separate out the fiber. Finally, the protein and endosperm related components are separated based on density through countercurrent rinsing and centrifugation to separate the starch from the protein/gluten stream. The isolated starch stream is then extensively rinsed to remove any non-granular starch related solubles, including solubles such as inorganic salts, and compounds such as phytate and salts of phytic acid. The resulting product is a highly purified slurry of insoluble granular starch which serves as the starting product for conversion to fructose.

In general, starch to fructose processing consists of four steps: liquefaction of granular starch, saccharification of the liquefied starch into dextrose, purification, and isomerization to fructose. The object of a starch liquefaction process is to convert a concentrated suspension of starch polymer granules into a solution of soluble shorter chain length dextrins of low viscosity. This step is essential for convenient handling with standard equipment and for efficient conversion to glucose or other sugars. To liquefy granular starch, it is necessary to gelatinize the granules by raising the temperature of the granular starch to over about 72° C. The heating process instantaneously disrupts the insoluble starch granules to produce a water soluble starch solution. The solubilized starch solution is then liquefied by α-amylase (EC 3.2.1.1.).

A common enzymatic liquefaction process involves adjusting the pH of a granular starch slurry to between 6.0 and 6.5, the pH optimum of α-amylase derived from *Bacillus licheniformis*, with the addition of calcium hydroxide, sodium hydroxide or sodium carbonate. The addition of calcium hydroxide has the advantage of also providing calcium ions which are known to stabilize the α-amylase against inactivation. Upon addition of α-amylase, the suspension is pumped through a steam jet to instantaneously raise the temperature to between 80°–115° C. The starch is immediately gelatinized and, due to the presence of α-amylase, depolymerized through random hydrolysis of α(1-4) glycosidic bonds by α-amylase to a fluid mass which is easily pumped.

In a second variation to the liquefaction process, α-amylase is added to the starch suspension, the suspension is held at a temperature of 80°–100° C. to partially hydrolyze the starch granules, and the partially hydrolyzed starch suspension is pumped through a jet at temperatures in excess of about 105° C. to thoroughly gelatinize any remaining granular structure. After cooling the gelatinized starch, a second addition of α-amylase can be made to further hydrolyze the starch.

A third variation of this process is called the dry milling process. In dry milling, whole grain is ground and combined with water. The germ is optionally removed by flotation separation or equivalent techniques. The resulting mixture, which contains starch, fiber, protein and other components of the grain, is liquefied using α-amylase. The general practice in the art is to undertake enzymatic liquefaction at a lower temperature when using the dry milling process. Generally, low temperature liquefaction is believed to be less efficient than high temperature liquefaction in converting starch to soluble dextrins.

Typically, after gelatinization the starch solution is held at an elevated temperature in the presence of α-amylase until a DE of 10–20 is achieved, usually a period of 1–3 hours. Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100.

The maximum temperature at which the starch solution containing α-amylase can be held depends upon the microbial source from which the enzyme was attained and the molecular structure of the α-amylase molecule. α-amylases produced by wild-type strains of *B. subtilis* or *B. amyloliquefaciens* are typically used at temperatures no greater than about 90° C. due to excessively rapid thermal inactivation above that temperature, whereas α-amylases produced by wild-type strains of *B. licheniformis* can be used at temperatures up to about 110° C.

The presence of starch and calcium ion are known to stabilize α-amylases against inactivation. Nonetheless, α-amylases are used at pH values above 6 to protect against rapid inactivation. At low temperatures, α-amylase from *B. licheniformis* is known to display excellent hydrolyzing activity on starch substrate at pH values as low as 5. However, when the enzyme is used for starch hydrolysis at common jet temperatures, e.g., between 102° C. and 109° C., the pH must be maintained at least above pH 5.7 to avoid excessively rapid inactivation. The pH requirement unfortunately provides a narrow window of processing opportunity because pH values above 6.0 result in undesirable by-products, e.g., maltulose. Therefore, in reality, liquefaction pH must be maintained between 5.9 and 6.0 to attain a satisfactory yield of hydrolyzed starch.

Another problem relating to pH of liquefaction is the need to raise the pH of the starch suspension from about 4, the pH of a corn starch suspension as it comes from the wet milling stage, to 5.9–6.0. This pH adjustment requires the costly addition of acid neutralizing chemicals and also requires additional ion-exchange refining of the final starch conversion product to remove the chemical. Moreover, the next process step after liquefaction, typically saccharification of the liquefied starch into glucose, requires a pH of 4–4.5; therefore, the pH must be adjusted down from 5.9–6.0 to 4–4.5; requiring additional chemical addition and refining steps.

In U.S. Pat. No. 5,322,778, liquefaction between pH 4.0 and 6.0 was achieved by adding an antioxidant such as bisulfite or a salt thereof, ascorbic acid or a salt thereof, erythorbic acid, or phenolic antioxidants such as butylated hydroxyanisole, butylated hydroxytoluene, or α-tocopherol to the liquefaction slurry. According to this patent, the antioxidant must be added in a concentration of greater than 5 mM.

In U.S. Pat. No. 5,180,669, liquefaction between a pH of 5.0 to 6.0 was achieved by the addition of carbonate ion in excess of the amount needed to buffer the solution to the ground starch slurry. Due to an increased pH effect which occurs with addition of carbonate ion, the slurry is generally neutralized by adding a source of hydrogen ion, for example, an inorganic acid such as hydrochloric acid or sulfuric acid.

In PCT Publication No. WO 94/02597, a mutant α-amylase having improved oxidative stability is described wherein one or more methionines are replaced by any amino acid except cysteine or methionine.

In PCT publication No. 94/18314; a mutant-amylase having improved oxidative stability is described wherein one or more of the methionine, tryptophan, cysteine, histidine or tyrosine residues is replaced with a non-oxidizable amino acid.

In PCT Publication No. WO 91/00353, the problems associated with liquefaction are approached by genetically engineering α-amylase to include characteristics including increased thermal, acid and alkaline stability.

In U.S. Pat. No. 4,914,029, phytase is added to the corn steep liquor to reduce the quantity of phytic acid in the corn steep liquor, and thus more efficiently utilize the corn steep liquor in animal feed.

Despite the advances made in the prior art, a continuing need exists for efficient means for starch liquefaction at low pH levels using commercially available α-amylase.

SUMMARY OF THE INVENTION

It is an object of this invention to provide improved efficiency low pH liquefaction of starch using readily available mutant or wild-type α-amylase enzymes.

It is a further object of this invention to provide a method of liquefying starch without the addition of costly antioxidants.

According to the present invention a method for liquefying aqueous starch comprising the steps of: (a) adding a sodium composition in a concentration greater than 20 ppm to the starch; (b) adding α-amylase to the starch; and (c) incubating the starch comprising the sodium composition and the α-amylase for a time and under conditions suitable to liquefy the starch to form a liquefied starch solution; whereby step (c) is carried out under conditions such that the starch comprises less than 5 mM of an anti-oxidant. According to a preferred embodiment of the invention, the sodium composition is present in a concentration of about 20 ppm or greater; preferably from about 20 ppm to about 10,000 ppm; more preferably from about 50 ppm to about 1000 ppm; and most preferably from about 100–500 ppm. Also preferably, step (c) is carried out at a pH of less than about 5.9; more preferably less than about 5.7; and most preferably less than about 5.5.

As pointed out in greater detail below, practice of the present invention confers important advantages to commercial starch liquefaction processes. While not wishing to be bound by theory, Applicants believe that the addition of a sodium composition counteracts problems associated with low pH liquefaction of starch with α-amylase because of either an increase in the stability of the enzyme itself or from the reaction of sodium with a composition or compositions in the starch solution which destabilizes the starch. Applicants' surprising discovery that the addition of sodium confers increased low pH activity to α-amylase permits efficient liquefaction of granular starch at pH values below about 5.9 with commercially available α-amylases.

The invention itself, together with further objects and attendant advantages, will best be understood by reference to the following detailed description taken in conjunction with the accompanying drawings.

DETAILED DESCRIPTION OF THE INVENTION

"Liquefaction" or "liquefy" means a process by which starch is converted to shorter chain and less viscous dextrins. Generally, this process involves gelatinization of starch simultaneously with or followed by the addition of α-amylase. In commercial processes, it is preferred that the granular starch is derived from a source comprising corn, wheat, milo, sorghum, rye or bulgher. However, the present invention applies to any grain starch source which is useful in liquefaction, e.g., any other grain or vegetable source known to produce starch suitable for liquefaction.

"Steep liquor" means a liquid which is drawn from steeped grain kernels during the sleeping process. The steep liquor contains a significant portion of the soluble components of the grain.

"Granular starch" or "starch granules" means a water-insoluble component of edible grains which remains after removal of the hull, fiber, protein, fat, germ, and solubles through the steeping, mechanical cracking, separations, screening, countercurrent rinsing and centrifugation steps typical of the grain wet-milling process. Granular starch comprises intact starch granules containing, almost exclusively, packed starch molecules (i.e., amylopectin and amylose). In corn, the granular starch component comprises about 99% starch; the remaining 1% being comprised of protein, fat, ash, fiber and trace components tightly associated with the granules. The packing structure of granular starch severely retards the ability of α-amylase to hydrolyze starch. Gelatinization of the starch is utilized to disrupt the granules to form a soluble starch solution and facilitate enzymatic hydrolysis.

"Starch solution" means the water soluble gelatinized starch which results from heating granular starch. Upon heating of the granules to above about 72° C., granular starch dissociates to form an aqueous mixture of loose starch molecules. This mixture comprising, for example, about 75% amylopectin and 25% amylose in yellow dent corn forms a viscous solution in water. In commercial processes to form glucose or fructose, it is the starch solution which is liquefied to form a soluble dextrin solution.

"α-Amylase" means an enzymatic activity which cleaves or hydrolyzes the α(1-4) glycosidic bond, e.g., that in starch, amylopectin or amylose polymers. Suitable α-amylases are the naturally occurring α-amylases as well as recombinant or mutant amylases which are useful in liquefaction of starch. Preferred amylases in the present invention are α-amylases derived from Bacillus, and particularly *Bacillus licheniformis*, *Bacillus amyloliquefaciens* or *Bacillus stearothermophilus*.

"Sodium composition" or "sodium" means a composition or mixture containing sodium which, when dissolved in aqueous solution, results in the presence of free sodium ion.

Sodium compositions may be free sodium ion, sodium metal, sodium containing salts or any other art recognized method for introducing free sodium ion into an aqueous solution. Suitable sodium salts include sodium chloride, sodium bicarbonate, sodium benzoate, sodium sulfate, sodium bisulfite, sodium ascorbate, sodium acetate, sodium nitrate, sodium tartrate, sodium tetraborate, sodium propionate, sodium citrate, sodium succinate, monosodium glutamate, trisodium citrate, sodium phosphate or a mixture thereof.

The concentration of the sodium composition should generally be a concentration which is sufficient to permit the efficient liquefaction of starch according to the present invention. Generally, the concentration of the sodium containing composition added to the starch is 20 ppm or greater; preferably from about 20 ppm to about 10,000 ppm; more preferably from about 50 ppm to about 1000 ppm; and most preferably from about 100–500 ppm.

Liquefaction of the starch according to the present invention allows the liquefaction reaction, i.e., enzymatic hydrolysis of the starch, amylopectin or amylose, to be carried out efficiently at a pH of less than 5.9, or even less than 5.5, in contrast to prior art liquefaction methods. Preferably the liquefaction reaction is carried at a pH of less than 5.9; more preferably between about 4.5 and about 5.7; and most preferably between about 4.5 and about 5.5.

The temperature range of the liquefaction is generally any liquefaction temperature which is known to be effective in liquefying starch. Preferably, the temperature of the starch is between about 80° C. to about 115° C., more preferably from about 100° C. to about 110° C., and most preferably from about 105° C. to about 108° C.

In a preferred embodiment of the invention, a sodium containing compound is added to a granular starch or a starch solution prior to or simultaneously with the addition of α-amylase and liquefaction of the starch. The slurry is then incubated for an appropriate time at an appropriate pH and at an appropriate temperature, according to well known techniques, to liquefy the starch. According to the present invention, the ability to efficiently liquefy starch is substantially improved by adding the sodium composition to the starch solution prior to liquefaction, i.e., prior to the addition of α-amylase.

The following examples are representative, and not limitative, of the advantages conferred through the use of the invention. However, one of ordinary skill in the art would be able to substitute conditions, grains, temperature, enzymes and the like according to the above disclosure.

EXAMPLES

Example 1

Assay for α-Amylase Activity Determination

α-Amylase activity was determined through an assay which depends on the ability of starch to form a blue colored complex with iodine and the disappearance of this color when starch is hydrolyzed to shorter dextrin molecules. The α-amylase activity was defined in terms of the digestion time required to produce a color change denoting a definite state of dextrination of the starch.

Reagents used were as follows: Phosphate buffer—Potassium dihydrogen phosphate (340 g) and sodium hydroxide (25.3 g) were dissolved in water and diluted to ~2 liters. The buffer was cooled to room temperature and the pH was adjusted to 6.2±0.1. The buffer was diluted to 2 liters in a volumetric flask. Starch substrate—Ten grams (dry substance) of soluble lintner starch were suspended in 50 ml of water and washed into ~300 ml of boiling water. The suspension was again brought to boiling and was boiled for 5 minutes with constant stirring. The starch solution was cooled with constant stirring to room temperature and 125 ml of phosphate buffer was added. The solution was diluted to 500 ml with water. Stock iodine solution—iodine crystals (5.5 g) and potassium iodide (11.0 g) were dissolved in water and were volumetrically diluted to 250 ml. The solution was kept from light. Dilute iodine solution—Potassium iodide (20 g) and 2 ml of stock iodine solution were dissolved in water and diluted volumetrically to 500 ml. Enzyme diluting solution—Calcium chloride (11.1 g) was dissolved in 4 liters of water. Water used for all reagents was either distilled or deionized.

The α-amylase sample for which the activity was to be determined was diluted to between 10–15 LU/ml (as defined below) with enzyme diluting solution. For many commercial α-amylase preparations a suitable dilution was found to be 2000 fold. Five milliliter aliquots of dilute iodine solution were dispensed into 13×100 mm test tubes and 10 ml of starch substrate was placed in a 23×200 mm test tube. All tubes were placed in the 30° C. water bath. A Hellige comparator equipped with a special α-amylase color disc (catalog number 620-s5) was used to make readings. Five milliliters of diluted enzyme (also at 30° C.) were mixed with the starch substrate and timing was begun. At appropriate time intervals, for Example 1 minute intervals early in the reaction and 15 second intervals later in the reaction, 1 ml aliquots of the enzyme-substrate mixture were transferred to a tube containing the attemperated dilute iodine solution. The starch iodine solution was mixed and transferred to a 13 mm precision square tube and the color was compared with the standard α-amylase color disc in the Hellige comparator. When the time of the end point was approached, samples were taken at 0.25 minute intervals.

The time required for the colors of the samples and the color disc to match were recorded and the activity (in liquefons per gram or ml) was calculated according to the formula:

$$LU/g \text{ or } LU/ml = \left\{ \frac{570}{V \times t} \right\} \times D$$

Where
LU=liquefon unit
V=volume of enzyme (5 ml)
t=dextrinization time (minutes)
D=dilution factor: dilution volume divided by the milliliters or grams of enzyme diluted.

Example 2

Starch Liquefaction Conditions—Determination of Liquefied Starch DE (Dextrose Equivalent)

Starch liquefaction was performed using a reactor composed of 50 feet of 0.24 inch diameter (0.21 inch i.d.) stainless steel tubing bent into an approximately 10 inch diameter coil ~5.5 inches high. The coil was equipped with an 11.5 inch in-line static mixer (Cole-Parmer #G-04669-60) mounted ~4 feet from the anterior end. The posterior end of the coil was equipped with a Swagelok in-line adjustable pressure relief value (#SS-4CA-3) set at a cracking pressure of about 20 psi. Starch slurry was fed to the coil at a rate of ~70 ml/minute with a piston metering pump. The coil was heated by immersion in a glycerol-water bath heated to 105.5° C. Temperature in the bath was maintained using a circulating heater\temperature controller (Fisher Scientific model 7305).

Granular starch was obtained from a corn wet miller and used within two days. As another source of starch, LO-DEX™ 10 (a water-soluble purified dextrin produced by the limited hydrolysis of corn starch), was purchased from American Maize-Products Company, Hammond, Ind. The LO-DEX™ 10 used herein had an initial DE of ~9.5.

The starch or maltodextrin was diluted to a desired solids level of about 30–35% dry solids with deionized water and the pH was adjusted with 2.5% NaOH or 6% HCl as required. Calcium was added in the form of $CaCl_2.2H_2O$. Typical liquefaction conditions were:

| Starch or LO-DEX ™ 10 | 32%–35% solids |
|---|---|
| Calcium | 40–60 ppm (30 ppm added) |
| pH | 5.0–6.0 |
| α-Amylase | 12–14 LU/g of carbohydrate (dry basis) |

Starch or LO-DEX™ 10 containing enzyme and calcium in the form of $CaCl_2.2H_2O$ was introduced into the reactor at about 70 ml/min. The temperature of the reactor was held at 105.5° C. by immersion of the reactor in a glycerol-water bath. Samples of starch were transferred from the reactor to a 95° C. second stage liquefaction bath and held for 90 minutes. The degree of starch liquefaction was measured immediately after the second stage liquefaction by determining the dextrose equivalent (DE) of the sample according to the method described in the *Standard Analytical Methods of the Member Companies of the Corn Refiners Association, Inc.*, sixth ed., Analytical Procedure Committee (1980).

Alternatively, starch was liquefied using a hydroheater M 103-M steam jet (Hydro-Thermal Corp., Milwaukee, Wis.) equipped with a 2.5 liter delay coil behind the mixing chamber and a terminal back pressure valve. Starch was fed to the jet at approximately 360 ml/min by a Moyno pump and steam was supplied by a 150 psi steam line reduced to 90–100 psi and controlled to yield a slurry temperature of about 105.5° C. measured at the rear temperature probe. Temperature probes were installed approximately 10 cm after the Hydroheater jet and approximately 5 cm before the back pressure valve.

Example 3

Effect of Cations on the Liquefaction of Corn Starch at Low pH by α-Amylase

Dried corn starch (Clinton Brand 106-B Pearl corn starch, ADM Corn Processing, Clinton, Iowa) was slurried with deionized water (~23 kg in ~50 liters) and allowed to hydrate for 16 hours. The starch was washed twice by filtration and resuspension in deionized water to remove soluble materials and then diluted to 35% solids with deionized water. Calcium (50 ppm added as $CaCl_2.2H_2O$) was added to the starch and the pH was adjusted to approximately 5.5 with 2.5% NaOH. Approximately 5 mM of the cation to be evaluated was added to the starch slurry and α-amylase (SPEZYME AA20, produced by a strain of *B. licheniformis* and available commercially from Genencor International, Inc.) was added at a rate of 12 LU/g carbohydrate and the pH of the solution was adjusted to pH 5.5 by the addition of 2.5% NaOH or 6% HCl as required. The solution was hydrolyzed using the reactor system and procedure as described in Example 2. The degree of hydrolysis of the starch slurry was measured by determining the dextrose equivalent (DE) immediately following the secondary hold.

The following table shows that the inactivation of α-amylase during liquefaction of corn starch at pH 5.5 is prevented by the addition of sodium salts, but not by other cations.

TABLE 1

| Effect of Cations on Corn Starch Liquefaction at pH 5.5 | |
|---|---|
| Chemical Evaluated | DE |
| None | 4.9 |
| NaCl | 9.7 |
| LiCl | 3.0 |
| KCl | 6.5 |
| $NH_4Cl$ | 5.3 |
| $(NH_4)_2SO_4$ | 5.4 |
| $CaCl_2$ | 5.1 |

Applicants verified that small effects seen with certain cations (i.e., $K^+$ and $NH_4^+$) were consistent with small variations in the amount of NaOH added for pH adjustment. Nonetheless, Applicants believe that a small effect is also provided by potassium ion, e.g. approximately 10–25% of that caused by a sodium composition.

Example 4

The Effect of Varying the Counter Anion on Sodium Stabilization of α-Amylase

Dried corn starch (Clinton Brand 106-B Pearl corn starch, ADM Corn Processing, Clinton, Iowa) was slurried with deionized water (~23 kg in ~50 liters) and allowed to hydrate for 16 hours. The starch was washed twice by filtration and resuspension in deionized water to remove soluble materials and then diluted to 35% solids with deionized water. Calcium (50 ppm added as $CaCl_2.2H_2O$) was added to the starch and the pH was adjusted to approximately 5.5 with 5% KOH. Various sodium salts were added to the starch slurry to give final sodium concentrations of 5 mM. α-Amylase (SPEZYME AA20, produced by a strain of *B. licheniformis* and available commercially from Genencor International, Inc.) was added at a rate of 12 LU/g carbohydrate and the pH of the solution was adjusted to pH 5.5 by the addition of 5% KOH or 6% HCl as required. The solution was hydrolyzed using the reactor system and procedure as described in Example 2. The degree of hydrolysis of the starch slurry was measured by dextrose equivalent (DE) immediately following the secondary hold.

As shown in Table 2, the inactivation of α-amylase during liquefaction of corn starch at pH 5.5 is prevented by the addition of sodium ion from a variety of sources. While sodium bromate apparently was ineffective, this is attributed to the strong oxidation effect known to occur between bromate and protein.

TABLE 2

| Effect Of Sodium Ion On α-Amylase Stability During Liquefaction At pH 5.5 | |
|---|---|
| Sodium Salt Evaluated | DE |
| None | 2.3 |

TABLE 2-continued

Effect Of Sodium Ion On α-Amylase Stability During Liquefaction At pH 5.5

| Sodium Salt Evaluated | DE |
|---|---|
| NaH$_2$PO$_4$ | 8.9 |
| Sodium Benzoate | 11.7 |
| Na$_2$SO$_4$ | 10.7 |
| NaNO$_3$ | 10.8 |
| Potassium Sodium Tartrate | 9.8 |
| Sodium Tetraborate | 10.7 |
| Sodium Propionate | 11.2 |
| Sodium Citrate | 6.6 |
| Sodium Succinate | 10.4 |
| Mono-Sodium Glutamate | 10.6 |
| Sodium Bromate | ~0 |

Example 5

Effect of Sodium Ion and α-Amylase Concentration on Corn Starch Liquefaction

A corn starch slurry from a corn wetmilling plant was diluted to 35% solids with deionized water and 30 ppm calcium was added as Ca(OH)$_2$. Various sodium ion concentrations were added to the starch slurry to yield the desired sodium ion concentration. At least two sodium ion concentrations were evaluated at each α-amylase concentration. The concentration of sodium ion in the starch slurry was measured by sodium ion electrode (Corning #476138). The starch slurry of known solids was filtered through Whatman #3 filter paper and the sodium concentration of the filtrate was measured as described in the sodium electrode manual. Sodium ion concentrations are reported as parts per million of the whole starch slurry.

The pH of the starch slurry was adjusted to about the desired pH (between 5.5 and 5.9) with 5% KOH or 6% HCl as required. α-Amylase (SPEZYME AA20, produced by a strain of B. licheniformis and available commercially from Genencor International, Inc.) was added at a rate of 12, 15 or 18 LU/g carbohydrate dry solids and the pH of the solution was adjusted to the desired pH by the addition of 5% KOH or 6% HCl as required. The solution was hydrolyzed using the steam jet and procedure as described in Example 2. The degree of hydrolysis of the starch slurry was measured by dextrose equivalent (DE) immediately following the secondary hold.

The sodium ion concentrations used in the liquefactions were adjusted so that DE's above and below 10 were obtained at each α-amylase dosage evaluated. The sodium ion concentration required to produce a DE 10 liquefied starch at each enzyme dosage was then determined by plotting the DE values vs. the sodium ion concentrations and interpolating between the data points.

As shown in Table 3, as the pH of liquefaction drops or as the α-amylase concentration is lowered, more sodium ion is required to produce a DE 10 liquefied starch.

TABLE 3

Sodium Concentration Required to Produce a DE10 Liquefact

| | Sodium Concentration (ppm) | | |
|---|---|---|---|
| pH | 12 LU/g | 15 LU/g | 18 LU/g |
| 5.9 | 100 | 28 | 5 |
| 5.7 | 155 | 95 | 22 |
| 5.5 | 322 | 200 | 63 |

Of course, it should be understood that a wide range of changes and modifications can be made to the preferred embodiment described above. It is therefore intended that the foregoing detailed description be understood that it is the following claims, including all equivalents, which are intended to define the scope of this invention.

We claim:

1. A method for liquefying a starch slurry comprising the steps of:
   (a) adding a sodium composition to said starch slurry, wherein a final sodium concentration of said starch slurry is present in a concentration greater than 20 ppm;
   (b) adding α-amylase to said starch slurry; and
   (c) incubating said starch slurry with said sodium composition and said α-amylase for a time and under conditions suitable to liquefy said starch to form a liquefied starch solution;
   whereby said step (c) is carried out under conditions such that an anti-oxidant is present in said starch slurry in a concentration less than 5 mM.

2. The method according to claim 1, wherein said sodium composition comprises sodium chloride, sodium bicarbonate, sodium benzoate, sodium sulfate, sodium bisulfite, sodium ascorbate, sodium acetate, sodium nitrate, sodium tartrate, sodium tetraborate, sodium propionate, sodium citrate, sodium succinate, monosodium glutamate, trisodium citrate, sodium phosphate or a mixture thereof.

3. The method according to claim 1, wherein said sodium composition is present in a final concentration of from about 20 ppm to about 10,000 ppm.

4. The method according to claim 1, wherein said sodium composition is present in a final concentration of from about 50 ppm to about 1000 ppm.

5. The method according to claim 1, wherein said sodium composition is present in a final concentration of from about 100 ppm to about 500 ppm.

6. The method according to claim 1, wherein said step (c) is at a pH of less than about 5.9.

7. The method according to claim 1, wherein said step (c) is at a pH between about 4.5 and about 5.7.

8. The method according to claim 1, wherein said step (c) is at a pH of between about 4.5 and about 5.5.

9. The method according to claim 1, wherein said step (a) is prior to said step (b).

10. The method according to claim 1, wherein said step (a) is simultaneous with said step (b).

* * * * *